United States Patent [19]

Cohen et al.

[11] 4,178,361
[45] Dec. 11, 1979

[54] SUSTAINED RELEASE PHARMACEUTICAL COMPOSITION

[75] Inventors: Arthur I. Cohen; James S. Y. Sim; Maurice H. Van Horn; Stanley E. Gordesky; Stanley I. Gordon, all of Rochester, N.Y.

[73] Assignee: Union Corporation, Verona, Pa.

[21] Appl. No.: 636,494

[22] Filed: Dec. 1, 1975

Related U.S. Application Data

[63] Continuation of Ser. No. 395,861, Sep. 10, 1973, abandoned.

[51] Int. Cl.² ............................................. A61K 9/22
[52] U.S. Cl. ..................................... 424/22; 424/81
[58] Field of Search .............................. 424/19–22

[56] References Cited

U.S. PATENT DOCUMENTS

| | | | |
|---|---|---|---|
| 2,659,732 | 11/1953 | Cusic et al. | 260/335 |
| 2,776,299 | 1/1957 | Cusic et al. | 260/328 |
| 2,830,930 | 4/1958 | Olinger | 424/310 |
| 3,232,833 | 1/1966 | Riviere | 424/183 |
| 3,551,556 | 12/1970 | Kliment et al. | 424/21 |
| 3,577,512 | 5/1971 | Shepherd et al. | 424/21 |
| 3,584,113 | 6/1971 | Takebe et al. | 424/19 |
| 3,641,237 | 2/1972 | Gould et al. | 424/16 |
| 3,673,612 | 7/1972 | Merrill et al. | 3/1 |
| 3,765,414 | 10/1973 | Arlen | 128/260 |
| 3,826,678 | 7/1974 | Hoffman et al. | 117/81 |
| 3,844,989 | 10/1974 | Harumiya et al. | 260/17.4 R |

OTHER PUBLICATIONS

Stecher et al., Merck Index, 8th ed., 1968, p. 671, "Methantheline Bromide".

Primary Examiner—Shep K. Rose
Attorney, Agent, or Firm—Pollock, Vande Sande & Priddy

[57] ABSTRACT

A sustained release pharmaceutical composition which includes a pharmacological material; a biological binding agent for the pharmacological material; and a matrix of a water-insoluble but water-swellable hydrophilic polymer.

14 Claims, No Drawings

SUSTAINED RELEASE PHARMACEUTICAL COMPOSITION

This is a continuation of application Ser. No. 395,861, filed Sept. 10, 1973 now abandoned.

BACKGROUND OF THE INVENTION

The present invention is concerned with a sustained release pharmaceutical composition, and in particular is concerned with a sustained release pharmaceutical composition which contains a pharmacological material; a binding agent for the pharmacological material; and a matrix of a water-insoluble but water-swellable hydrophilic polymer. The present invention is also concerned with methods for preparing the pharmaceutical compositions.

It has previously been suggested to incorporate drugs into hydrophilic polymers to provide sustained release of the drug. However, the particular drugs which have to date been satisfactorily employed in such a sustained release mechanism are very limited since not every combination of a drug and any type of hydrophilic polymer provides a suitable slow release mechanism. Furthermore, such systems are not very susceptible to tailoring the release for a particular application. That is, the slowing down or speeding up of a release system is not readily accomplished. In addition, many prior suggested sustained release pharmaceutical compositions require relatively large quantities of synthetic materials.

Accordingly, it is an object of the present invention to make it possible to provide sustained release pharmaceutical compositions which are applicable for a large variety of pharmacological agents. Another object of the present invention is to provide a means by which it is possible to selectively alter the release characteristics for a particular application. A further object of the present invention is a reduction in the quantity of synthetic materials without a concomitant reduction in the release characteristics of the pharmacological compositions.

SUMMARY OF THE INVENTION

The present invention is concerned with a sustained release pharmaceutical composition comprising a pharmacological material in an amount at least sufficient for the total dosage requirement during the treatment period; a biological binding agent for the pharmacological agent, wherein the biological binding agent contains bonding sites complementary to bonding sites of the pharmacological material in an amount effective to bind the pharmacological material and to provide for the sustained release of said pharmacological material in the desired dosage amount; a matrix of a water-insoluble but water-swellable hydrophilic polymer which holds the biological binding agent; and wherein the molecular size or weight of the biological binding agent is sufficient to cause retention of said biological binding agent in the matrix and to prevent egress of the biological binding agent from the matrix during the treatment period.

The present invention is also directed to a method of preparing the above-described sustained release pharmaceutical composition which comprises admixing a monomeric composition being polymerizable to form a water-insoluble but water-swellable hydrophilic polymer and the biological binding agent; polymerizing the monomeric mixture to form a matrix of a water-insoluble but water-swellable hydrophilic polymer having dispersed therein the biological binding agent; and then adding to the resultant product pharmacological material in an amount at least sufficient for the total dosage requirement during the treatment period.

The present invention is also concerned with a process for preparing the sustained release pharmaceutical compositions as discussed above which comprises contacting the pharmacological material with the biological binding agent to bond the pharmacological material to the biological binding agent; admixing the resulting composition with a monomeric composition being polymerizable to a water-insoluble but water-swellable hydrophilic polymer; and polymerizing to provide the sustained release pharmaceutical composition as defined above.

DESCRIPTION OF PREFERRED EMBODIMENTS

The pharmacological material employed according to the present invention can be any material suitable for treating the body, both human and animal, and includes any composition or substance that will produce a pharmacological response. Generally the molecular weight of the pharmacological material is less than about 10,000 and preferably less than about 5,000. Most of the pharmacologicl materials have molecular weights of 1,000 or less. Some non-limiting examples of pharmacological materials include anti-infectives such as nitrofurazone, sodium propioniate, antibiotics, including penicillin, tetracycline, oxytetracycline, chlorotetracycline, bacitracin, nystatin, streptomycin, neomycin, polymyxin, gramicidin, chloramphenicol, ad erythromycin; sulfonamides, including sulfacetamide, sulfamethizole, sulfamethazine, sulfadiazine, sulfamerazine, and sulfisoxazole; and anti-virals including idoxuridine; antiallergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; vaccines such as smallpox, yellow fever, distemper, hog cholera, chicken pox, antivenom, scarlet fever, dyptheria toxoid, tetanus toxoid, pigeon pox, whooping cough, influenzae, rabies, mumps, measles, poliomyelitis, and Newcastle disease; decongestants such as phenylephrine, naphazoline, and tetrahydrazoline; miotics and anticholinesterases such as pilocarpine, esperine salicylate, carbachol, diisopropyl fluorophosphate, phospholine iodide, and demacarium bromide; parasympatholytics such as atropine sulfate, cyclopentolate, hematropine, scopolamine, tropicamide, eucatropine, and hydroxyamphetamine; sympathomimetics such as epinephrine; sedatives and hypnotics such as pentabarbital sodium, phenobarbital, secobarbital sodium, codeine, (α-bromoisovaleryl) urea, carbromal; psychic energizers such as 3-(2-aminopropyl) indole acetate and 3-(2-aminobutyl) indole acetate; tranquilizers such as reserpine, chlorpromayline, and thiopropazate; androgenic steroids such as methyltestosterone and fluorymesterone; estrogens such as estrone, 17 β-estradiol, ethinyl estradiol, and diethyl stilbesterol; progestational agents such as progesterone, megestrol, melengestrol, chlormadinone, ethisterone, norethynodrel, 19-norprogesterone, norethindrone, medroxyprogesterone and 17 β-hydroxy-progesterone;

humoral agents such as the prostaglandins, for example $PGE_1$, $PGE_2$ and $PGF_2$; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine; antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; nutritional agents such as vitamins.

Other pharmacological materials having the same or different physiological activity as those recited above can be employed in the present invention. The pharmacological materials can be in various forms, such as uncharged molecules, components of molecular complexes, or nonirritating, pharmacologically acceptable salts such as succinate, hydrochloride, hydrobromide, sulfate, phosphate, nitrate, borate, acetate, maleate, tartrate, salicylate, and the like. For acidic drugs, salts of metals, amines or organic cations (e.g., quaternary ammonium) can be employed. Furthermore, simple derivatives of the pharmacological materials (such as ethers, esters, amides, etc.) which have desirable retention and release characteristics but which are easily hydrolyzed by body pH, enzymes, and the like can be employed.

The amount of pharmacological material employed in the pharmaceutical compositions of the present invention can vary greatly and is primarily dependent upon the effectiveness of the particular pharmacological material, and the desired pharmacological effect. Accordingly, there is no real upper critical limitation nor lower critical limitation upon the amount of pharmacological material. The particular quantity of a pharmacological agent to be employed in the present invention can readily be determined by those skilled in the art once they are aware of the present invention.

The substance employed according to the present invention which binds the pharmacological material to prevent immediate release and to provide for sustained release of the pharmacological material is a biological binding agent. The biological binding agents contain bonding sites which are complementary to bonding sites of the pharmacological material. That is, the biological binding agent contains bonding sites which interact with bonding sites present on the pharmacological material to bind or hold the pharmacological material. The complementary bonding sites of the pharmacological material and biological binding agent are of the type which are capable of providing for a sustained release of the pharmacological material of the desired dosage, and in particular provide an attractive force or bridge between the pharmacological material and biological binding agent so that the biological binding agent holds the pharmacological material as opposed to merely acting as a physical barrier such as an encapsulating layer for the pharmacological material. Included among the bonds employed according to this invention are ionic bonds, hydrogen bonds and hydrophobic bonds including van der Waals' forces. Examples of some pharmacological material—biological binding agent systems containing such complementary sites include the pharmacological material containing cations and the biological binding agent containing anions; the pharmacological material containing anions and the biological binding agent containing cations; both the pharmacological material and the biological binding agent containing polar moieties; and both the pharmacological material and the biological binding agent being hydrophobic or containing hydrophobic sites. The degree to which a particular pharmacological material is bound can be manipulated by selection of the biological binding agent and, in some instances, by the conditions of adding the pharmacological material and biological binding agent. The degree of bonding will in turn effect the release characteristics of the pharmacological agent.

It is understood that the biological binding agents suitable from the present invention include both natural and synthetic biological substances; conjugates thereof; and derivatives including polymers thereof. Illustrative of derivatives are crosslinked biological materials such as the dextrans crosslinked with crosslinking agents such as epichlorohydrin, methylenebis acrylamide, cyanuric chloride, divinyl sulfone, bis epoxides (ie. methylene bis epoxide), and bis aldehydes (ie. terephthaldehyde); pharmacologically acceptable salts such as succinate, hydrochloride, phthalate, hydrobromide, sulfate, phosphate, nitrate, borate, acetate, maleate, tartrate, and the like; esters; ethers; amides; and the like. The biological binding agents employed according to the present invention have molecular weights of at least about 300 and usually at least about 10,000. The molecular weight of the biological binding agent should be higher than the pharmacological material bound thereto.

Exemplary of suitable biological binding agents include proteins, peptides, nucleic acids, carbohydrates, lipids, conjugates thereof and mixtures thereof.

The proteins which can be employed in the present invention can be simple proteins which contain only amino acids or can be conjugated proteins which contain amino acids plus other substances such as nucleic acids, carbohydrates, lipids, and the like. Included among the proteins which can be employed in the present invention are nucleoprotein, glycoprotein and phosphoproteins. Generally the proteins have molecular weights from about 6,000 to about 4,000,000. Preferably the molecular weight of the proteins is between about 10,000 and about 100,000. Some examples of proteins include albumins such as ovalbumin, and bovine or human serumalbumin; myoglobin; 3-lactoglobulin; hemoglobin; rennin; papain; prolamines such as zein; glutelins such as gluten; scleroproteins such as collagen, gelatin, elastins and keratins; protamines; histones; and phosphoproteins such as casein and vitellin. Other examples of protein-like biological binders include polymers of biological amino acids such as arginine, glutamic acid, asparatic acid, lysine, phenylalanine, tryptophan and the like.

Another group of biological binding agents for the pharmacological material are the carbohydrates including the polysaccharides. Generally the carbohydrates have molecular weights from about 1,000 to about 400 million and preferably from about 1000 to about 100,000. Some examples of suitable carbohydrates include glycogen, cellulose, pentosans and hexosans, such as araban, xylans, dextrans, and mannan; pectins, alginic acid, Chitin, inulin, agar, hyaluronic acid, ovomucoid heparin and chondroitin sulfate.

Another group of suitable biological binding agents for the pharmacological materials are the lipids including the phospholipids, glycolipids and proteolipids. Some specific examples of suitable lipids are lecithins, cephalins, sphinogomyelins, and cardiolipins. Preferably the fatty acid portions of lecithins, cephalins and sphinogomyelins are fatty acids containing about 12 to about 22 carbon atoms. The proteolipids generally have molecular weights from about 6,000 to about 4,000,000; and preferably from about 10,000 to about 100,000; whereas, the phospholipids generally have molecular weights from about 500 to to about 1500. The molecular weight of the glycolipids is usually from about 1000 to about 400 million and preferably from about 1000 to about 100,000.

The nucleic acids include ribonucleic acids and deoxyribonucleic acids; and generally have molecular weights of at least about 1000 and preferably about 10,000 to about 100,000.

The peptides include polypeptides and have molecular weights generally from about 500 to about 6,000.

The other essential constituent of the pharmaceutical compositions of the present invention is the water-insoluble but water-swellable hydrophilic polymer.

The water-insoluble but water-swellable polymers are obtained from a hydrophilic monomer and a cross-linking agent. Generally the cross-linking agent is present in an amount from about 0.05 to about 60% by weight, and preferably from about 0.1 to about 40% by weight. Some suitable examples of hydrophilic monomers include hydroxy lower alkyl acrylates or methacrylates, or hydroxy lower alkoxy lower alkyl acrylates or methacrylates such as 2-hydroxy ethyl acrylate, 2-hydroxy ethyl methacrylate, diethylene glycol monoacrylate, diethylene glycol monomethacrylate, 2-hydroxy propyl acrylate, 2-hydroxy propyl methacrylate, 3-hydroxy propyl acrylate, 3-hydroxy propyl methacrylate, and dipropylene glycol monomethacrylate. Other suitable hydrophilic monomers include the heterocyclic polymerizable compounds containing a carbonyl functionality adjacent to the nitrogen in the heterocyclic ring such as the N-vinyl lactams, N-vinyl imidazolidones, N-vinyl succinimide, N-vinyl diglycolylimide, N-vinyl glutarimide, N-vinyl-3-morpholinone, N-vinyl-5-methyl-3-morpholinone. Usually the heterocyclic compounds contain from about 3 to 6 carbon atoms in the ring. Examples of some contemplated N-vinyl lactams include N-vinyl-2-pyrrolidone, N-vinyl-2-piperidone, and N-vinyl-e-caprolactam.

Illustrative of some crosslinking agents are ethylene glycol diacrylate, ethylene glycol dimethacrylate, 1,2-butylene dimethacrylate, 1,3-butylene dimethacrylate, 1,4-butylene dimethacrylate, propylene glycol diacrylate, propylene glycol dimethacrylate, diethylene glycol dimethacrylate, dipropylene glycol dimethacrylate, diethylene glycol diacrylate, dipropylene glycol diacrylate, tetraethylene glycol dimethacrylate, glycidyl acrylate, glycidyl crotonate, divinyl benzene, divinyl toluene, diallyl tartrate, allyl pyruvate, allyl maleate, divinyl tartrate, triallyl melamine, N,N'-methylene bisacrylamide, glycerine trimethacrylate, diallyl maleate, divinyl ether, diallyl monoethylene glycol citrate, ethylene glycol vinyl allyl citrate, allyl vinyl maleate, diallyl itaconate, ethylene glycol diester of itaconic acid, divinyl sulfone, hexahydro-1,3,5-triacryltriazine, triallyl phosphite, diallyl ester of benzene phosphonic acid, polyester of maleic anhydride with triethylene glycol, polyallyl glucose, such as triallyl glucose, polyallyl sucrose, such as pentaallyl sucrose, sucrose diacrylate, glucose dimethacrylate, pentaerythritol tetraacrylate, sorbitol dimethacrylate, diallyl aconitrate, divinyl citraconate, diallyl fumarate, and glycidyl methacrylate.

The preferred crosslinking agents include divinyl benzene, glycidyl acrylate, glycidyl methacrylate, and glycidyl crotonate. Some examples of suitable polymers which include glycidyl methacrylate, glycidyl acrylate, and/or glycidyl crotonate as the crosslinking agent are disclosed in U.S. patent applications Ser. Nos. 186,821; 186,822; and 187,131, all filed on Oct. 5, 1971, the entire disclosures of which are incorporated herein by reference. Illustrative of such polymers which include glycidyl acrylate, glycidyl methacrylate and/or glycidyl crotonate as a crosslinking agent are as follows:

I. Water insoluble but water swellable copolymer of a monomer mixture of:
  (A) a heterocyclic polymerizable compound containing a carbonyl functionality adjacent to the nitrogen in the heterocyclic ring, and being selected from the group consisting of N-vinyl lactams, N-vinyl imidazolidone, N-vinyl succinimide, N-vinyl diglycolylimide, N-vinyl glutarimide, N-vinyl-3-morpholinone, N-vinyl-5-methyl-3-morpholinone, and mixtures thereof; and preferably N-vinyl-2-pyrrolidone;
  (B) glycidyl methacrylate, and/or glycidyl acrylate, and/or glycidyl crotonate; and wherein the monomer mixture contains from about 40 to about 75% and preferably from 50 to about 65% by weight of the heterocyclic polymerizable compound, and from about 25 to about 60% and preferably from about 35 to about 50% by weight of the glycidyl ester based upon the total weight of (A) and (B) in the monomer mixture.

II. Water insoluble but water swellable copolymer of a monomer mixture of:
  (A) heterocyclic polymerizable compound containing a carbonyl functionality adjacent to the nitrogen in the heterocyclic ring and being selected from the group consisting of N-vinyl lactams, N-vinyl imidazolidone, N-vinyl succinimide, N-vinyl diglycolylimide, N-vinyl glutarimide, N-vinyl-3-morpholinone, N-vinyl-5-methyl-3-morpholinone, and mixtures thereof; and preferably being N-vinyl-pyrrolidone.
  (B) monoethylenically unsaturated esters selected from the group consisting of alkyl acrylates, alkyl methacrylates, vinyl esters of saturated monocarboxylic acids of up to 22 carbon atoms, and mixtures thereof, wherein the alkyl group of said methacrylate or acrylate contains from 1 to 22 carbon atoms; and
  (C) glycidyl esters selected from the group consisting of glycidyl methacrylate, glycidyl acrylate, glycidyl crotonate, and mixtures thereof; and
wherein the monomer mixture contains from about 50 to about 90% by weight of (A), from about 5 to about 40% by weight of (B) and from about 0.5 to about 30% by weight of (C) based upon the total weight of (A), (B), and (C) in the monomer mixture.

The monomer mixture preferably contains from about 60 to about 80% by weight of (A), from about 25 to about 35% by weight of (A), and from about 2.5 to about 15% by weight of (C) based upon the total weight of (A), (B), and (C) in the monomer mixture, and most preferably contains from about 60 to about 70% by weight of (A), from about 25 to about 30% by weight of (B), and from about 4 to about 12% by weight of (C) based upon the total weight of (A), (B), and (C) in the monomer mixture.

III. Bulk polymerized water insoluble but water swellable copolymer of a monomer mixture of:
  (A) a polymerizable monoester of acrylic acid and/or methacrylic acid and a polyhydric alcohol, such as hydroxyethyl methacrylate, hydroxyethyl acrylate, hydroxypropyl methacrylate, and hydroxypropyl acrylate; and
(B) glycidyl acrylate and/or glycidyl methacrylate and/or glycidyl crotonate; and wherein the monomer mixture contains based upon the total weight of the polymerizable monoester and the glycidyl ester from 60 to 99.75% and preferably from about 85 to about 97.5% of the polymerizable monoester and from 0.25 to 40% and preferably from about 2.5 to about 15% of the glycidyl ester.

Another specific group of polymers include water insoluble but water swellable copolymers of a monomer mixture of
(A) a polymerizable monoester of acrylic and/or methacrylic acid and a polyhydric alcohol such as hydroxyethyl methacrylate, hydroxypropyl methacrylate, and hydroxypropyl acrylate; and
(B) a crosslinking agent such as divinyl benzene, divinyl toluene, or a polymerizable diester of acrylic and/or methacrylic acid and a polyhydric alcohol such as ethylene glycol diacrylate, ethylene glycol dimethacrylate, 1,2-butylene dimethacrylate, 1,3-butylene dimethacrylate, 1,4-butylene dimethacrylate, diethylene glycol dimethacrylate, dipropylene glycol dimethacrylate, diethylene glycol diacrylate, dipropylene glycol diacrylate, tetraethylene glycol dimethacrylate, and tetraethylene glycol diacrylate; wherein the monomer mixture contains based upon the total weight of the polymerizable monoester and crosslinking agent from about 80% to about 99.95% and preferably from about 90% to about 99.9% by weight of the monoester and from about 0.05 to about 20% and preferably from about 0.1 to about 10% by weight of the crosslinking agent.

Illustrative of other polymers include water-insoluble but water-swellable copolymers of a monomer mixture of:
(A) a heterocyclic polymerizable compound containing a carbonyl functionality adjacent to the nitrogen in the heterocyclic ring, and being selected from the group consisting of N-vinyl lactams, N-vinyl imidazolidone, N-vinyl succinimide, N-vinyl diglycolylimide, N-vinyl glutarimide, N-vinyl-3-morpholinone, N-vinyl-5-methyl-3-morpholinone, and mixtures thereof; and preferably N-vinyl-2-pyrolidone;
(B) monoethylenically unsaturated esters selected from the group consisting of alkyl acrylates, alkyl methacrylates, vinyl esters of saturated monocarboxylic acids of up to 22 carbon atoms, and mixtures thereof, wherein the alkyl group of said methacrylate or acrylate contains from 1 to 22 carbon atoms; and
(C) a crosslinking agent such as divinyl benzene, divinyl toluene, or a polymerizable diester of acrylic and/or methacrylic acid and a polyhydric alcohol such as ethylene glycol diacrylate, ethylene glycol dimethacrylate, 1,2-butylene dimethacrylate, 1,3-butylene dimethacrylate, 1,4-butylene dimethacrylate, diethylene glycol dimethacrylate, dipropylene glycol dimethacrylate, diethylene glycol diacrylate, dipropylene glycol diacrylate, tetraethylene glycol dimethacrylate, and tetraethylene glycol diacrylate;
wherein the monomer mixture contains based upon the total weight of heterocyclic polymerizable compound, unsaturated ester, and crosslinking agent, from about 90 to about 45% by weight and preferably from about 80 to about 55% by weight of the heterocyclic polymerizable compound, from about 5 to about 50% by weight and preferably from about 15 to about 45% by weight of the unsaturated ester; and from about 0.5% to about 15% by weight and preferably from about 1% to about 10% by weight of the crosslinking agent.

Generally the pharmacological material is employed in amounts of about 0.1 to about 50% and preferably from about 0.5 to about 20% by weight based on the total weight of the pharmacological material, biological binding agent, and the water-insoluble but water-swellable hydrophilic polymer. The amount of biological binding agent for the pharmacological material must be sufficient to adequately bond the pharmacological material to provide a sustained release of the pharmacological material in the desired dosage amount, and is generally from about 1 to about 80% by weight and preferably from about 20 to about 60% by weight based upon the total weight of pharmacological material, biological binding agent, and water-swellable hydrophilic polymer. The water-insoluble but water-swellable hydrophilic polymer is generally employed in amounts of at least about 10% and preferably about 35 to about 60% by weight based upon the total weight of pharmacological material, biological binding agent, and hydrophilic polymer.

In addition, the pharmaceutical compositions of the present invention can include such other materials as suspending aids for the pharmacological material or biological binder including Cab-O-Sil and bentone; plasticizers, and inert fillers.

Moreover, the pharmaceutical compositions of the present invention can be further encapsulated by another polymeric or other film-forming substance according to particular applications of the pharmaceutical composition. Such auxiliary encapsulating layers can be soluble or insoluble in aqueous medium, the solubility or swelling being dependent or independent of pH and/or ionic strength, and can be susceptible or non-susceptible to enzymatic action.

The pharmaceutical compositions of the present invention can be prepared by admixing a mixture of monomeric materials which are polymerizable to the water-insoluble but water-swellable polymer and the biological binder for the pharmacological material. The resulting composition is then polymerized to provide a matrix of a water-insoluble but water-swellable hydrophilic polymer retaining or holding the biological binder for the pharmacological material. After the polymerization, the pharmacological agent is contacted with the resulting composition in such a manner as to be sorbed into the matrix of the water-swellable polymer and to be bound to the biological binding agent to thereby provide a slow release pharmaceutical composition. In particular, the combination of the biological binding agent and the matrix of water-insoluble polymer can be impregnated with the pharmacological material by immersion in a bath such as an aqueous bath of the pharmacological material to cause the pharmacological material to diffuse into the matrix and be bound by the biological binding agent. In some instances, it may be desirable to employ a liquid diluent (i.e., an alcohol) with the binding agent to facilitate mixing with the monomers.

Generally the pharmacological material is contacted with the biological binder for at least about 15 minutes to cause bonding. Of course, this can vary greatly depending upon the relative amounts of the ingredients including the amount of matrix material, and the affinity of the pharmacological material and biological binder for each other.

Moreover, the pharmaceutical compositions of the present invention can be prepared by initially contacting the pharmacological material with the biological binding agent therefor to achieve bonding between the pharmacological material and biological binding agent. Then, either the resulting composition can be admixed with a monomer mixture polymerizable to the water-insoluble but water-swellable polymer followed by polymerization or can be encapsulated or coated with an already polymerized water-insoluble polymer. In either case, the resultant product is a matrix of the water-insoluble but water-swellable polymer containing the biological binding agent having the pharmacological material bound to the biological binding agent.

The water-swellable polymers employed in the present invention generally can be prepared by employing bulk polymerization techniques. The term "bulk polymerization" as used herein includes those polymerizations carried out in the absence of a solvent or dispersing liquid as well as those polymerizations carried out in the presence of water or water-soluble or polymer-soluble liquid swelling agents in such amounts as not to significantly alter the nature of the polymerization process.

The polymerization catalyst employed can be any of the catalysts which are suitable in polymerizing compounds containing ethylenic unsaturation and preferably are the free radical catalysts. Of particular interest are the peroxide catalysts. Some examples of suitable peroxide catalysts include hydrogen peroxide, benzoyl peroxide, tert-butyl peroctoate, phthalic peroxide, succinic peroxide, benzoyl acetic peroxide, tert-butyl peroxypivalate, coconut oil acid peroxide, lauric peroxide, stearic peroxide, oleic peroxide, tert-butyl hydroperoxide, tetraline hydroperoxide, tert-butyl diperphthalate, cumene hydroperoxide, tert-butyl perbenzoate, acetyl peroxide, 2,4-dichlorobenzoyl peroxide, urea peroxide, caprylyl peroxide, p-chlorobenzoyl peroxide, ditert-butyl peroxide, 2,2-bis(tert-butyl peroxy)-butane, hydroxyheptyl peroxide, the diperoxide of benzaldehyde; alkylperoxycarbonates such as diisobutylperoxy bicarbonate, di-secondary butyl peroxy bicarbonate, and tert-butyl peroxyisopropylcarbonate, and the like. The preferred catalyst is one which is effective at moderately low temperatures such as at about 30°–90° C.

When the crosslinking agent is a glycidyl compound such as glycidyl methacrylate, it may be desirable that the catalyst in addition to containing the free radical polymerization catalyst may include a material which accelerates polymerization primarily by opening of the epoxide group of the glycidyl ester. Such catalysts include p-toluene sulphonic acid, sulfuric acid, phosphoric acid, aluminum chloride, stannic chloride, ferric chloride, boron trifluoride, boron trifluoride-ethyl ether complex, and iodine. Also, when the crosslinking agent includes a glycidyl compound, it may be desirable to employ a multistage polymerization process. For instance, the polymerization can initially be conducted until substantially all of the unsaturated groups have polymerized, and then can be conducted to effect polymerization through the breaking of the oxirane group of the glycidyl ester and condensation.

The amount of catalyst employed depends upon the type of catalyst system used and is generally from about 0.01 to about 10 parts by weight per 100 parts of the monomer mixture, and preferably is from about 0.1 to about 1 part by weight per 100 parts of the monomer mixture.

The polymerization is generally carried out at temperatures from about room temperature to about 150° C. It is generally preferred to initiate the polymerization at relatively low temperatures such as from about 35° to about 85° C., and then to increase the temperature to about 90° to about 150° C. as the reaction proceeds and preferably after most of the reaction has been completed. The most preferred initial temperature range of polymerization is between about 30° and 90° C.

Usually the polymerization is conducted under autogenous pressure in a closed reaction vessel. However, any suitable means to prevent significant evaporation of any of the monomers can be employed.

Generally, the polymerization is completed in about one-half to about 12 hours and preferably is completed in about 4 to about 6 hours. It is understood, of course, that the time and temperature are inversely related. That is, temperatures employed at the upper end of the temperature range will provide polymerization processes which can be completed near the lower end of the time range.

In addition, it may be desirable for the copolymers obtained from such polymerizations to be post cured at temperatures somewhat higher than those initially employed in the polymerization. Usually the temperatures employed in the post cure will range from about 90° to about 150° C. Two hours is usually more than sufficient for such a post curing operation. Preferably the post cure is completed in 2 to 4 hours.

The pharmaceutical compositions of the present invention can be utilized for oral ingestion, implantation, or external application to the skin or a mucous membrane. The pharmaceutical compositions of the present invention can be implanted subcutaneously, constitute a part of a prosthesis, or be inserted in a cavity of the human body. Upon application to the desired part of the body by the desired mode, the pharmaceutical compositions of the present invention provide sustained release of the pharmacological material by allowing it to diffuse through pores of the water insoluble but water-swellable polymeric matrix to the desired part of the body upon contact with body fluids. In addition, the biological binding agent is retained by the matrix of the water-insoluble but water-swellable polymer during the treatment period.

The present invention makes it possible to obtain a sustained release pharmaceutical composition employing a biological material as the binding agent for the pharmacological material, which would not be achieved without all of the essential components of this invention. For instance, the water-insoluble but water-swellable polymeric matrix protects the biological binding agent so as to at least significantly retard and in many cases prevent deterioration of the biological binding agent when the composition is in contact with the part of the body being treated. For instance, the matrix protects biological binding agents employed in the present invention from being digested during the treatment period when the pharmaceutical composition is taken orally. Digestion of the biological binding agent, of course, would defeat the main purpose of the present invention of providing a sustained release preparation.

Furthermore, when the pharmaceutical composition is employed by implantation or external application to the skin or a mucous membrane, the matrix prevents the undesirable formation of antibodies in the treated area, which could occur if the biological binding agent were in direct contact with the body. Accordingly, the presence of the matrix of the water insoluble but water swellable polymer is essential in providing a practical and useful sustained release pharmaceutical composition containing a biological binding agent.

In addition, the present invention makes it possible to better control the sustained release characteristics of the pharmacological material. For instance, the biological binding agent can be selected for a particular pharmacological material to provide a rate of release desired for a particular application of the preparation. This control or tailoring of the rate of release is achievable since the biological binding agent actually binds the pharmacological material in the manner previously described and since the strength of the bond between a particular biological binding agent and different pharmacological materials can vary. This effect is quite different from systems wherein the material used to regulate the release of the pharmacological material merely acts as a physical barrier and does not bind the pharmacological material according to the present invention. For instance, a particular physical barrier would release all pharmacological materials of similar molecular size at substantially the same rate. In addition, the matrix and amount thereof can be selected so as to slow down the rate of release in addition to the protection functions discussed above.

Moreover, the present invention makes it possible to employ lesser relative quantities of non-biological materials based upon the amount of pharmacological material than generally used in preparing sustained release pharmaceutical compositions.

The following non-limiting examples are provided to further illustrate the present invention. All parts are by weight unless the contrary is stated.

EXAMPLE 1

An albumin-containing composition is prepared by admixing 15.46 parts of albumin, 3.21 parts of Cab-O-Sil EH5 and 81.33 parts of a polymerizable composition containing about 58.4% by weight of N-vinyl-2-pyrrolidone, 40.0% by weight of methyl methacrylate, 1% by weight of divinylbenzene and 0.6% of t-butyl peroxypivalate. The mixture is heated to 45° C. for about 12 hours under a nitrogen atmosphere of 20 psi to effect polymerization.

About 100 parts of the resulting polymeric composition are soaked for about 12 hours at ambient temperature in about 5000 parts of an isotonic saline solution (0.9% NaCl) containing 100 mg of methantheline bromide per 5 ml of saline solution. The above composition is introduced into a beaker containing 20 milliliters of isotonic saline (0.9% NaCl) and the beaker is shaken at a constant temperature of 37° C. in a thermostatic water bath shaker. The concentration of eluted methantheline is determined with a Beckman DB-GT spectrophotometer using the maximum absorption of methantheline bromide at 282 nanometers (nm). Elution rates are checked at the time intervals shown in Table 1 and fresh isotonic saline is employed after each reading. The results are listed below in Table 1.

EXAMPLE 2

Example 1 is repeated except that the polymer-albumin composition is soaked for about 12 hours in an isotonic saline solution (0.9% NaCl) containing 100 mg of chlorpheniramine maleate per 5 ml saline solution. The concentration of eluted chlorpheniramine maleate is determined with a Beckman DB-GT spectrophotometer using the maximum absorption of chlorpheniramine maleate at 262 nm. The results are listed below in Table 1.

EXAMPLE 3

Example 1 is repeated except that the polymer-albumin composition is soaked for about 12 hours in an isotonic saline solution (0.9% NaCl) containing 100 mg of prednisolone-21-sodium succinate per 5 ml of saline solution. The concentration of eluted prednisolone-21-succinate is determined with a Beckman DB-GT spectrophotometer using the maximum absorption of prednisolone-21-sodium succinate at 242 nm. The results are listed below in Table 1.

TABLE I

| Time (hours) | Methantheline (Example 1) Percent of Total Eluted | Chlorpheniramine Maleate (Example 2) Percent of Total Eluted | Prednisolone 21 Succinate (Example 3) Percent of Total Eluted |
|---|---|---|---|
| 1 | 48.1 | 53.0 | 36.3 |
| 2 | 15.3 | 16.5 | 13.2 |
| 3 | 9.9 | 10.2 | 8.6 |
| 4 | 6.7 | 6.25 | 4.5 |
| 5 | 4.9 | 4.3 | 3.8 |
| 6 | 3.9 | 3.1 | 4.1 |
| 7 | 3.0 | 2.2 | 3.35 |
| 24 | 7.8 | 4.2 | 17.1 |
| 25 | 0.5 | 0.25 | 1.1 |
| 26 | — | — | 0.7 |
| 48 | — | — | 4.8 |
| 72 | — | — | 1.75 |
| 74 | — | — | 0.2 |
| 80 | — | — | 0.25 |
| 96 | — | — | 0.5 |

EXAMPLE 4

A heparin-containing composition is prepared by admixing 8.81 parts of heparin, 2.59 parts of Cab-O-Sil EH5 and 88.6 parts of a polymerizable composition containing about 99.1% by weight of hydroxyethylmethacrylate, 0.5% by weight of divinylbenzene and 0.4% of t-butyl peroctoate. The mixture is heated to 54° C. for about 12 hours under a nitrogen atmosphere to effect polymerization.

About 100 parts of the resulting polymeric composition are soaked for about 12 hours at ambient temperature in about 5000 parts of an isotonic saline solution (0.9% NaCl) containing 100 mg of methantheline bromide per 5 ml of saline solution. The above composition is introduced into a beaker containing 20 milliliters of isotonic saline solution (0.9% NaCl) and the beaker is shaken at a constant temperature of 37° C. in a thermostatic water bath shaker. The concentration of eluted methantheline is determined with a Beckman DB-GT spectrophotometer using the maximum absorption of methantheline bromide at 282 nanometers. Elution rates are checked at the intervals shown in Table II and fresh isotonic saline is employed after each reading. The results are listed below in Table II.

EXAMPLE 5

Example 4 is repeated except that the polymer-heparin composition is soaked for about 12 hours in an isotonic saline solution (0.9% NaCl) containing 100 mg of pilocarpine HCl per 5 ml of saline solution. The concentration of eluted pilocarpine is determined with a Beckman DB-GT spectrophotometer using the maximum absorption of pilocarpine at 215 nm. The results are listed below in Table II.

EXAMPLE 6

Example 5 is repeated except that the polymer-heparin composition is soaked for 12 hours in an isotonic saline solution (0.9% NaCl) containing 100 mg of atropine sulfate per 5 ml of saline solution. The concentration of eluted atropine is determined with a Beckman DB-GT spectrophotometer using the maximum absorption of atropine sulfate at 205 nm. The results are listed below in Table II.

TABLE II

| Time (hours) | Methantheline (Example 4) Percent of Total Eluted | Pilocarpine (Example 5) Percent of Total Eluted | Atropine (Example 6) Percent of Total Eluted |
|---|---|---|---|
| 1 | 39.9 | 85.53 | 69.26 |
| 2 | 13.9 | 10.15 | 18.06 |
| 3 | 9.5 | 2.80 | 8.44 |
| 4 | 7.1 | 1.52 | 4.24 |
| 5 | 5.5 | — | — |
| 6 | 4.9 | — | — |
| 7 | 3.9 | — | — |
| 24 | 13.3 | — | — |
| 25 | 1.4 | — | — |
| 26 | 0.6 | — | — |

Table II demonstrates how the selection of a particular pharmacological material and biological binding agent can after the bonding characteristics and in turn regulate the release properties. This demonstrates that pilocarpine HCl and atropine sulfate have a different affinity for the heparin than does the methantheline bromide.

EXAMPLE 7

A zein-containing composition is prepared by admixing 7.76 parts of zein, 15.37 parts of methanol and 76-87 parts of a polymerizable composition containing about 58.4% by weight of N-vinyl-2-pyrrolidone, 40.0% by weight of methyl methacrylate, 1% by weight of divinylbenzene and 0.6% of t-butyl peroxypivalate. The mixture is heated to 40° C. for about 12 hours under a nitrogen atmosphere to effect polymerization. The composition is then post cured by heating at 100° C. for about 2 hours at atmospheric pressure.

About 80 parts of the resulting polymer composition are soaked for about 12 hours at ambient temperature in about 5000 parts of an isotonic saline solution (0.9% NaCl) containing 101.1 mg of methantheline bromide. The above composition is introduced into a beaker containing 20 milliliters of isotonic saline solution (0.9% NaCl) and the beaker is shaken at a constant temperature of 37° C. in a thermostatic water bath beaker. The concentration of eluted methantheline is determined with a Beckman DB-GT spectrophotometer using the maximum absorption of methantheline bromide at 282 nm. Elution rates are checked at the time intevals shown in Table III and fresh isotonic saline is employed after each reading. The results are listed below in Table III.

EXAMPLE 8

Example 7 is repeated except that the polymerzein composition is soaked for about 12 hours in an isotonic saline solution (0.9% NaCl) containing 100 mg of chlorpheniramine maleate per 5 ml saline solution. The concentration of eluted chlorpheniramine maleate is determined with a Beckman DB-GT spectrophotometer using the maximum absorption of chlorpheniramine maleate at 262 nm. The results are listed below in Table III.

TABLE III

| Time (hours) | Methantheline (Example 7) Percent of Total Eluted | Chlorpheniramine Maleate (Example 8) Percent of Total Eluted |
|---|---|---|
| 1 | 18.2 | 30.6 |
| 2 | 32.4 | 34.7 |
| 3 | 17.5 | 14.3 |
| 4 | 12.25 | 9.3 |
| 5 | 7.1 | 4.0 |
| 6 | 4.5 | 2.6 |
| 7 | 2.4 | 1.2 |
| 23.5 | 5.8 | 3.3 |
| 24 | — | — |

Comparison Example 9

Example 1 is repeated except that no albumin is employed. The results are listed in Table IV.

Comparison Example 10

Example 2 is repeated except that no albumin is employed. The results are listed in Table IV.

A comparison of Examples 9 and 10 with Examples 1 and 2, respectively, and with 7 and 8, respectively, shows the improved sustained release characteristics achieved by the present invention. In particular, a much greater percentage of the total pharmacological material released is released within the first hour when no biological binder is employed according to Examples 9 and 10 as compared to the percentage released within the first few hours when a biological binder is used according to the present invention.

TABLE IV

| Time (hours) | Methantheline (Example 9) Percent of Total Eluted | Chlorpheniramine Maleate (Example 10) Percent of Total Eluted |
|---|---|---|
| 1 | 54.4 | 69.5 |
| 2 | 16.7 | 15.9 |
| 3 | 9.25 | 6.6 |
| 4 | 5.9 | 3.3 |
| 5 | 4.2 | 2.0 |
| 7 | 4.4 | 1.6 |
| 24 | 3.8 | 1.1 |
| 25 | 1.5 | — |
| 27 | — | — |

The following examples are presented to demonstrate that the biological binders provide for the sustained release of the pharmacological compositions and to isolate the effect as much as possible from influence by the matrix. The following examples therefore employ dialysis bags in place of the matrix to negate the influence of the matrix on release. The dialysis bags employed are commercially available from VWR Scientific under the designation dialysis tubing and according to the manufacturer is seamless regenerated cellulose having an average pore radius of 25 angstroms. Further details of the dialysis bags can be found in Cat 25225-260 of VWR Scientific.

EXAMPLE 11

In a dialysis bag are placed 2 ml of an isotonic saline solution (0.9% NaCl) containing 100 mg of albumin. The bag is then placed for about 12 hours at ambient temperature in 30 ml of an isotonic saline solution (0.9% NaCl) containing 201.2 mg of methantheline bromide. The bag is then placed in 30 ml of isotonic saline solution (0.9% NaCl) at 37° C. The concentration of eluted methantheline is determined with a Beckman DB-GT spectrophotometer using the maximum absorption of methantheline bromide at 282 nm. Elution rates are checked at the time intervals shown in Table V. After each reading the bag is placed in fresh isotonic saline solution. The results are listed below in Table V.

EXAMPLE 12

Example 11 is repeated except that the bag is soaked for about 12 hours at ambient temperature in 30 ml of an isotonic saline solution (0.9% NaCl) containing 202.1 mg of chlorpheniramine maleate. The concentration of eluted chlorpheniramine maleate is determined with a Beckman DB-GT spectrophotometer using the maximum absorption of chlorpheniramine maleate at 262 nm. The results are listed below in Table V.

EXAMPLE 13

Example 11 is repeated except that the bag is soaked for about 12 hours at ambient temperature in 30 ml of an isotonic saline solution (0.9% NaCl) containing 206.8 mg of prednisolone-21-sodium succinate. The concentration of eluted prednisolone-21-succinate is determined with a Beckman DB-GT spectrophotometer using the maximum absorption of prednisolone-21-sodium succinate at 242 nm. The results are listed below in Table V.

TABLE V

| Time (hours) | Methantheline (Example 11) Percent of Total Eluted | Chlorpheniramine Maleate (Example 12) Percent of Total Eluted | Prednisolone-21-Succinate (Example 13) Percent of Total Eluted |
| --- | --- | --- | --- |
| 0.5 | 51.8 | 53.3 | 36.4 |
| 1.0 | 20.0 | 20.1 | 18.2 |
| 1.5 | 11.0 | 12.2 | 13.8 |
| 2.0 | 6.3 | 6.7 | 10.0 |
| 3.0 | 5.0 | 4.9 | 10.4 |
| 4.0 | 2.2 | 2.0 | 5.1 |
| 5.0 | 1.3 | 0.7 | 2.7 |
| 6.0 | 0.7 | 0.2 | 1.4 |
| 7.0 | 0.5 | — | 1.0 |
| 24.0 | 0.7 | — | 1.0 |

EXAMPLE 14

In a dialysis bag are placed 2.5 ml of an isotonic saline solution (0.9% NaCl) containing 100 mg of heparin. The bag is then placed for about 12 hours at ambient temperature in 45 ml of an isotonic saline solution (0.9% NaCl) containing 300 mg of methantheline bromide. The bag is then placed in 45 ml of isotonic saline solution (0.9% NaCl) at 37° C. The concentration of eluted methantheline is determined with a Beckman DB-GT spectrophotometer using the maximum absorption of methantheline bromide at 282 nm. Elution rates are checked at the time intervals shown in Table Vi. After each reading the bag is placed in fresh isotonic saline solution. The results are listed below in Table VI.

EXAMPLE 15

Example 14 is repeated except that the bag is soaked for about 12 hours at ambient temperature in 45 ml of an isotonic saline solution (0.9% NaCl) containing 300 mg of chlorpheniramine maleate. The concentration of eluted chlorpheniramine maleate is determined with a Beckman DB-GT spectrophotometer using the maximum absorption of chlorpheniramine maleate at 262 nm. The results are listed below in Table VI.

TABLE VI

| Time (hours) | Methantheline (Example 14) Percent of Total Eluted | Chlorpheniramine Maleate (Example 15) Percent of Total Eluted |
| --- | --- | --- |
| 0.5 | 34.0 | 35.4 |
| 1.0 | 22.0 | 21.8 |
| 1.5 | 15.0 | 15.2 |
| 2.0 | 10.75 | 10.8 |
| 2.5 | 5.9 | 5.5 |
| 3.5 | 6.6 | 6.35 |
| 4.5 | 2.9 | 2.7 |
| 5.5 | 1.3 | 1.2 |
| 7.5 | 0.8 | 0.8 |
| 23.5 | 0.3 | 0.25 |

EXAMPLE 16

In a dialysis bag are placed 2 ml of an isotonic saline solution (0.9% NaCl) containing 100 mg of gelatin. The bag is then placed for about 12 hours at ambient temperature in 30 ml of an isotonic saline solution (0.9% NaCl) containing 202.1 mg of chlorpheniramine maleate. The bag is then placed in 30 ml of isotonic saline solution (0.9% NaCl) at 37° C. The concentration of eluted chlorpheniramine maleate is determined with a Beckman DB-GT spectrophotometer using the maximum absorption of chlorpheniramine maleate at 262 nm. Elution rates are checked at the time intervals shown in Table VII. After each reading the bag is placed in fresh isotonic saline solution. The results are listed below in Table VII.

EXAMPLE 17

Example 16 is repeated except that the bag is soaked for about 12 hours at ambient temperature in 30 ml of an isotonic saline solution (0.9% NaCl) containing 206.8 mg of prednisolone-21-sodium succinate. The concentration of eluted prednisolone-21-succinate is determined with a Beckman DB-GT spectrophotometer using the maximum absorption of prednisolone-21-sodium succinate at 242 nm. The results are listed below in Table VII.

TABLE VII

| Time (hours) | Chlorpheniramine Maleate (Example 16) Percent of Total Eluted | Prednisolone-21-Succinate (Example 17) Percent of Total Eluted |
| --- | --- | --- |
| 0.5 | 66.8 | 47.6 |
| 1.0 | 19.1 | 21.3 |
| 1.5 | 8.7 | 13.7 |
| 2.0 | 3.4 | 7.8 |

TABLE VII-continued

| Time (hours) | Chlorpheniramine Maleate (Example 16) Percent of Total Eluted | Prednisolone-21-Succinate (Example 17) Percent of Total Eluted |
|---|---|---|
| 3.0 | 1.6 | 6.3 |
| 4.0 | 0.4 | 2.2 |
| 5.0 | — | 0.8 |
| 6.0 | — | 0.3 |

EXAMPLE 18

In a dialysis bag are placed 2.5 ml of an isotonic saline solution (0.9% NaCl) containing 100 mg of myoglobin. The bag is then placed for about 12 hours at ambient temperature in 45 ml of an isotonic saline solution (0.9% NaCl) containing 300 mg of methantheline bromide. The bag is then placed in 45 ml of isotonic saline solution (0.9% NaCl) at 37° C. The concentration of eluted methantheline is determined with a Beckman DB-GT spectrophotometer using the maximum absorption of methantheline bromide at 282 nm. Elution rates are checked at the time intervals shown in Table VIII. After each reading the bag is placed in fresh isotonic saline solution. The results are listed below in Table VIII.

EXAMPLE 19

Example 18 is repeated except that the bag is soaked for about 12 hours at ambient temperature in 45 ml of an isotonic saline solution (0.9% NaCl) containing 300 mg of chlorphreniramine maleate. The concentration of eluted chlorpheniramine maleate is determined with a Beckman DB-GT spectrophotometer using the maximum absorption of chlorpheniramine maleate at 238 nm. The results are listed below in Table VIII.

EXAMPLE 20

Example 18 is repeated except that the bag is soaked for about 12 hours at ambient temperature in 45 ml of an isotonic saline solution (0.9% NaCl) containing 300 mg of prednisolone-21-sodium succinate. The concentration of eluted prednisolone-21-succinate is determined with a Beckman DB-GT spectrophotometer using the maximum absorption of prednisolone-21-succinate at 242 nm. The results are listed below in Table VIII.

TABLE VIII

| Time (hours) | Methantheline (Example 18) Percent of Total Eluted | Chlorpheniramine Maleate (Example 19) Percent of Total Eluted | Prednisolone-21-Succinate (Example 20) Percent of Total Eluted |
|---|---|---|---|
| 0.5 | 48.2 | 52.3 | 34.4 |
| 1.0 | 25.4 | 22.6 | 20.6 |
| 1.5 | 13.5 | 12.8 | 15.9 |
| 2.0 | 6.7 | 6.7 | 10.3 |
| 2.5 | 2.8 | 2.7 | 6.3 |
| 3.5 | 2.4 | 2.1 | 7.2 |
| 4.5 | 0.6 | 0.4 | 3.0 |
| 5.5 | 0.2 | 0.4 | 1.5 |
| 7.5 | — | — | 0.9 |

EXAMPLE 21

In a dialysis bag are placed 2.5 ml of an isotonic saline solution (0.9% NaCl) containing 100 mg of chondroitin sulfate. The bag is then placed for about 12 hours at ambient temperature in 45 ml of an isotonic saline solution (0.9% NaCl) containing 300 mg of methantheline bromide. The bag is then placed in 45 ml of an isotonic saline solution (0.9% NaCl) at 37° C. The concentration of eluted methantheline is determined with a Beckman DB-GT spectrophotometer using the maximum absorption of methantheline bromide at 282 nm. Elution rates are checked at the time intervals shown in Table IX. After each reading the bag is placed in fresh isotonic saline solution. The results are listed below in Table IX.

EXAMPLE 22

Example 21 is repeated except that the bag is soaked for about 12 hours at ambient temperature in 45 ml of an isotonic saline solution (0.9% NaCl) containing 300 mg of chlorpheniramine maleate. The concentration of eluted chlorpheniramine maleate is determined with a Beckman DB-GT spectrophotometer using the maximum absorption of chlorpheniramine maleate at 262 nm. The results are listed below in Table IX.

TABLE IX

| Time (hours) | Methantheline (Example 21) Percent of Total Eluted | Chlorpheniramine Maleate (Example 22) Percent of Total Eluted |
|---|---|---|
| 0.5 | 29.2 | 32.8 |
| 1.0 | 25.1 | 19.8 |
| 1.5 | 15.1 | 13.9 |
| 2.0 | 12.3 | 13.1 |
| 2.5 | 6.2 | 7.8 |
| 3.5 | 6.5 | 6.5 |
| 4.5 | 3.1 | 3.2 |
| 5.5 | 1.5 | 1.5 |
| 7.5 | 0.9 | 1.0 |
| 23.5 | 0.3 | 0.4 |

Control Example 23

In a dialysis bag are placed 3 ml of an isotonic saline solution (0.9% NaCl) containing 17.66 mg of methantheline bromide. The bag is then placed in 30 ml of isotonic saline solution (0.9% NaCl) at 37° C. The concentration of eluted methantheline is determined with a Beckman DB-GT spectrophotometer using the maximum absorption of methantheline bromide at 282 nm. Elution rates are checked at the time intervals shown in Table X. After each reading the bag is placed in fresh isotonic saline solution. The results are listed below in Table X.

Control Example 24

Example 23 is repeated except that 3 ml of an isotonic saline solution (0.9% NaCl) containing 17.66 mg of chlorpheniramine maleate are placed in the dialysis bag. The concentration of eluted chlorpheniramine maleate is determined with a Beckman DB-GT spectrophotometer using the maximum absorption of chlorpheniramine maleate at 262 nm. The results are listed below in Table X.

Control Example 25

Example 23 is repeated except that 3 ml of an isotonic saline solution (0.9% NaCl) containing 18.07 mg of prednisolone-21-sodium succinate are placed in the dialysis bag. The concentration of eluted prednisolone-21-succinate is determined with a Beckman DB-GT spectrophotometer using the maximum absorption of prednisolone-21-sodium succinate at 242 nm. The results are listed below in Table X.

A comparison of Examples 23, 24, and 25 with Examples 11–22 illustrate that the biological binding agents are functioning to provide sustained release of the pharmacological material.

TABLE X

| Time (hours) | Methantheline (Example 23) Percent of Total Eluted | Chlorpheniramine Maleate (Example 24) Percent of Total Eluted | Prednisolone-21-Succinate (Example 25) Percent of Total Eluted |
|---|---|---|---|
| 0.5 | 57.5 | 74.8 | 73.5 |
| 1.0 | 23.6 | 18.2 | 19.4 |
| 1.5 | 11.0 | 5.1 | 5.2 |
| 2.0 | 4.6 | 1.5 | 1.5 |
| 2.5 | 1.9 | 0.4 | 0.4 |
| 3.0 | 1.0 | — | — |
| 3.5 | 0.5 | — | — |

What is claimed is:

1. A sustained release pharmaceutical composition comprising:
   (A) a pharmacological material in an amount at least sufficient for the total dosage during a treatment period;
   (B) a biological binding agent for said pharmacological material, said biological binding agent containing bonding sites complementary to bonding sites of the pharmacological material in an amount effective to bind the pharmacological materials and to provide for the sustained release of said pharmacological material in the desired dosage amount;
   (C) a matrix of a water-insoluble but water-swellable hydrophilic polymer, which holds said biological binding agent;
   (D) the molecular size or weight of the biological binding agent being sufficient to cause retention of said biological binding agent in said matrix and to prevent egress of said biological binding agent from said matrix during the treatment period.

2. The sustained release pharmaceutical composition of claim 1 wherein said pharmacological material is present in an amount from about 0.1 to about 50% by weight based upon the total weight of the pharmacological material, biological binding agent, and the water-insoluble but water-swellable hydrophilic polymer.

3. The sustained release pharmaceutical composition of claim 1 wherein said pharmacological material is present in an amount from about 0.5 to about 20% by weight based upon the total weight of the pharmacological material, biological binding agent, and the water-insoluble but water swellable hydrophilic polymer.

4. The sustained release pharmaceutical composition of claim 1 wherein said biological binding agent is a carbohydrate.

5. The sustained release pharmaceutical composition of claim 1 wherein the pharmacological material is bound to the biological binding agent by bonds which include ionic bonds, and/or hydrogen bonds, and/or hydrophobic bonds.

6. The sustained release pharmaceutical composition of claim 1 wherein the biological binding agent has a molecular weight of at least about 300.

7. The sustained release pharmaceutical composition of claim 1 wherein the biological binding agent is present in an amount from about 1 to about 80% by weight based upon the total weight of the pharmacological material, biological binding agent, and water-insoluble but water-swellable hydrophilic polymer.

8. The sustained release pharmaceutical composition of claim 1 wherein the biological binding agent is present in an amount from about 20 to about 60% by weight based upon the total weight of the pharmacological material, biological binding agent, and water-insoluble but water-swellable hydrophilic polymer.

9. The sustained release pharmaceutical composition of claim 1 wherein said water-insoluble but water-swellable polymer is a copolymer of a monomer mixture of:
   (A) a polymerizable monoester of acrylic and/or methacrylic acid and a polyhydric alcohol; and
   (B) a crosslinking agent selected from the group consisting of a divinyl benzene, divinyl toluene, a polymerizable diester of acrylic and/or methacrylic acid and a polyhydric alcohol, and mixtures thereof,
wherein the monomer mixture contains based upon the total weight of the polymerizable monoester and crosslinking agent from about 80% to about 99.95% by weight of the monoester and from about 0.05 to about 20% by weight of the crosslinking agent.

10. The sustained release pharmaceutical composition of claim 1 wherein said biological binding agent is heparin.

11. The sustained release pharmaceutical composition of claim 1 wherein said pharmacological material is methantheline bromide.

12. A process for preparing the sustained release pharmaceutical composition of claim 1 which comprises:
   (A) admixing a monomeric composition being polymerizable to form a water-insoluble but water-swellable hydrophilic polymer and a biological binding agent;
   (B) polymerizing the monomeric mixture to form a maxtrix of a water-insoluble but water-swellable hydrophilic polymer having dispersed therein the biological binding agent;
   (C) adding to the resultant product a pharmacological material in an amount at least sufficient for the total dosage requirement during a treatment period;
the molecular size or weight of the biological binding agent being sufficient to cause retention of said biological binding agent in said matrix and to prevent egress of said biological binding agent from said matrix during the treatment period.

13. A process for preparing the sustained release pharmaceutical composition of claim 1 which comprises:
   (A) contacting the pharmacological material and the biological binding agent to bond the pharmacological material to the biological binding agent;
   (B) admixing the resulting composition with a monomeric composition being polymerizable to a water-insoluble but water-swellable hydrophilic polymer;
   (C) polymerizing to form a matrix of a water-insoluble but water-swellable hydrophilic polymer having dispersed therein the biological binding agent; and
   (D) the molecular size or weight of the biological binding agent being sufficient to cause retention of said biological binding agent in said matrix and to prevent egress of said biological binding agent from said matrix during the treatment period.

14. The sustained release pharmaceutical composition of claim 1 wherein said pharmacological material is methantheline; said binding agent is heparin; and said water-insoluble but water-swellable hydrophilic polymer is a polymer of a monomer mixture of hydroxyethyl methacrylate and divinyl benzene wherein the monomer mixture contains based upon the total weight of the methacrylate and divinyl benzene from about 80% to about 99.95% by weight of the methacrylate and from about 0.05 to about 20% by weight of the divinyl benzene.

* * * * *